United States Patent [19]

Wagner

[11] Patent Number: 5,138,072
[45] Date of Patent: Aug. 11, 1992

[54] PROCESS FOR THE PREPARATION OF 5-CHLORO-3-CHLOROSULPHONYL-2-THIOPHENECARBOXYLIC ACID ESTERS

[75] Inventor: Hans P. Wagner, Itingen, Switzerland

[73] Assignee: Hafslund Nycomed Pharma Aktiengesellschaft, Linz, Austria

[21] Appl. No.: 800,702

[22] Filed: Dec. 2, 1991

Related U.S. Application Data

[63] Continuation of Ser. No. 609,061, Nov. 7, 1990, abandoned, which is a continuation of Ser. No. 337,885, Apr. 14, 1989, abandoned.

[30] Foreign Application Priority Data

May 2, 1988 [AT] Austria .................................. 1123/88

[51] Int. Cl.$^5$ ............................................ C07D 333/32
[52] U.S. Cl. ........................................................ 549/64
[58] Field of Search ............................................. 549/64

[56] References Cited

U.S. PATENT DOCUMENTS

| | | | |
|---|---|---|---|
| 2,168,260 | 8/1939 | Heisel et al. | 570/254 |
| 3,929,907 | 12/1975 | Janzon et al. | 549/81 |
| 4,028,373 | 6/1977 | Hromatka et al. | |
| 4,180,662 | 12/1979 | Pfister et al. | |
| 4,801,591 | 1/1989 | Binder . | |

FOREIGN PATENT DOCUMENTS 2159156 11/1985 United Kingdom .

OTHER PUBLICATIONS

Hartough, Thiophene & HS Derivatives (1932) pp. 147, 179.
Cohon, Adv. Inorg. Chem. 2nd Ed. (1966) p. 857.

Primary Examiner—Alan Siegel
Attorney, Agent, or Firm—Wenderoth, Lind & Ponack

[57] ABSTRACT

Process for the preparation of 5-chloro-3-chlorosulphonyl-2-thiophenecarboxylic acid esters by chlorination in the presence of activated iron.

6 Claims, No Drawings

PROCESS FOR THE PREPARATION OF 5-CHLORO-3-CHLOROSULPHONYL-2-THIO-PHENECARBOXYLIC ACID ESTERS

This application is a continuation of now abandoned application, Ser. No. 07/609,061 filed Nov. 7, 1990 which is a continuation of now abandoned Ser. No. 07/337,885, filed Apr. 14, 1989 abandoned.

The invention relates to a process for the preparation of 5-chloro-3-chlorosulphonyl-2-thiophenecarboxylic acid esters.

5-Chloro-3-chlorosulphonyl-2-thiophenecarboxylic acid alkyl esters (5-CCT) are intermediates in the preparation of pharmaceutically active substances. For example, blood fat-lowering substances which are prepared starting from 5-CCT are described in U.S. Pat. No. 4,801,591. The preparation of chlorotenoxicam (6-chloro-4-hydroxy-2-methyl-3-(2-pyridyl-carbamoyl)-2H-thieno(2,3-e)1,2-thiazine 1,1-dioxide), an antirheumatic, which is described in U.S. Pat. No. 4,180,662, can also be carried out starting from 5-CCT.

In GB-A 2,159,156, a process for the preparation of 3-chlorosulphonyl-2-thiophenecarboxylic acid alkyl esters substituted by methyl or halogen is described in which the only poorly accessible 5-chloro-3-amino-2-thiophenecarboxylic acid alkyl esters are diazotized and the diazonium chlorides formed are then reacted with $SO_2$ to give the sulphochlorides. However, this process is involved and gives only unsatisfactory yields.

The present invention relates to a process for the preparation of 5-chloro-3-chlorosulphonyl-2-thiophenecarboxylic acid esters of the formula

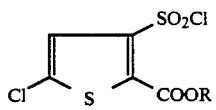   I in which R denotes $C_1$–$C_4$-alkyl, which is characterized in that a compound of the formula

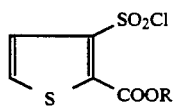   II in which R has the meaning above, is chlorinated in the presence of activated iron by introducing chlorine gas.

A method for the activation of the iron consists in suspending 0.1 to 1.0 mole, preferably 0.2–0.4 mole, of metallic iron in powder or turning form per mole of compound II in 0.5–5 l, preferably in 1–3 l, of organic solvent which is inert under the reaction conditions, such as, for example, methylene chloride, carbon tetrachloride or in mixtures of such solvents, methylene chloride being preferred. The iron is activated by introducing about 100–500 g, preferably about 200–300 g, of chlorine gas per mole of iron. The introduction of the chlorine gas is carried out with vigorous stirring of the iron suspension in the course of 1–5, preferably 2–3, hours at a temperature of about 10°–50° C., preferably 24°–28° C.

A further method of activation consists in initially introducing approximately equal amounts of iron, as described above, into a reaction flask and allowing the mixture to stand for 12 to 48 hours, preferably 24 hours, under a chlorine gas atmosphere. Activation of the iron in a solvent suspension is preferred, however.

For chlorination of 3-chlorosulphonyl-2-thiophenecarboxylic acid alkyl esters (CT), if the activation of the iron was carried out in a solvent suspension, CT is dissolved in the same solvent or solvent mixture in which the metallic iron was suspended, to be precise in about 0.3–5 l of solvent per mole of CT, preferably in 0.5 to 1 l of solvent per mole of CT and this solution is mixed rapidly with the iron suspension. The chlorination of the CT is carried out with stirring by introducing about 5–50 g of chlorine gas per hour and mole of CT, preferably 15–35 g per hour and mole of CT, at a temperature of about 20° to 50° C., preferably at a temperature of 30° to 32° C. The course of the reaction is in this case followed analytically, preferably by gas chromatography. After formation of 50–70%, preferably 62–65%, of monochloro compound, the reaction mixture is poured into ice water and the phases are separated. The organic phase is dried and evaporated.

If the activation of the iron was carried out under a chlorine gas atmosphere, CT is preferably dissolved in 2–4 l of one of the abovementioned solvents or solvent mixtures, and the course of the further chlorination is as described above. The total amount of solvent used is the same with both possibilities for activation.

The purification of the crude 5-CCT can be carried out in the usual ways, such as recrystallization, column and partition chromatography, extraction and the like. Recrystallization from diisopropyl ether is preferred.

The starting compound for the chlorination, CT, is known from the literature. Its preparation is described, for example, in U.S. Pat. No. 4,028,373.

EXAMPLE

Methyl 5-chloro-3-chlorosulphonylthiophene-2-carboxylate 96 g of iron powder (1.71 mol) (Baker, reduced by $H_2$, at least 96%) were suspended in 12 l of abs. methylene chloride in a 20 l four-necked flask. 440 g of chlorine gas were introduced with vigorous stirring in the course of 2 to 3 hours, during which the temperature was between 24° and 28° C. 1.44 kg (5.98 mol) of methyl 3-chlorosulphonylthiophenecarboxylate were then dissolved in 5 l of abs. methylene chloride and added rapidly. 100 to 200 g of chlorine gas per hour were introduced with stirring at a temperature of 30° to 32° C., and the course of the reaction was followed by means of gas chromatography. After formation of 62% to 65% of monochloro compound, the reaction mixture was poured into 24 l of ice water and stirred vigorously for 15 min. After separation of the phases, the organic phase was dried and the residue was evaporated in vacuo at 40° C. bath temperature.

The residue was taken up in 1.5 l of diisopropyl ether, filtered and the filtrate cooled to −30° to −35° C. After seeding with monochloro compound, the filtrate was allowed to crystallize for about 15 to 30 min. The crystallizate was filtered off with suction, washed with 0.5 l of diisopropyl ether at −30° C. and dried in a vacuum oven at 25° C.

Yield: 800 g of monochloro compound (48.7%) GC: 95% of monochloro compound, residue of unchlorinated and dichlorinated product.

M.p.: 50°–52° C.

I claim:

1. A process for the preparation of 5-chloro-3-chlorosulphonyl-2-thiophene-carboxylic acid esters of the formula

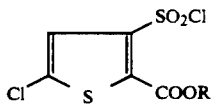

in which R denotes $C_1$–$C_4$-alkyl, which consists essentially of chlorinating the compound of the formula

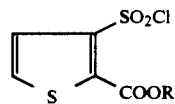

in which R has the meaning above, in the presence of activated iron in methylene chloride, by introducing chlorine gas until 50–70% of the desired 5-chloro-3-chlorosulphonyl-2-thiophene-carboxylic acid ester of formula I is formed, said activated iron being prepared by suspending 0.1 to 1.0 moles of metallic iron per mole of the compound of formula II in 0.5 to 5 l of methylene chloride and introducing 100–500 g of chlorine gas per mole of iron over 1 to 5 hours.

2. Process according to claim 1, which comprises activating the metallic iron with chlorine gas in a solvent suspension, 0.2–0.4 mole of metallic iron per mole of the compound of the formula II being suspended in 1–3 l of methylene chloride, and the iron being activated by introducing 200–300 g of chlorine gas per mole of iron during 2–3 hours.

3. Process according to claim 1, which comprises carrying out the chlorination of the compound of the formula II by introducing 5–50 g of chlorine gas per hour and mole of the compound of the formula II at 20° to 50° C. until 50–70% of the desired 5-chloro-3-chlorosulphonyl-2-thiophene-carboxylic acid ester are formed and then pouring the reaction mixture into ice water.

4. Process according to claim 1, which comprises carrying out the chlorination of the compound of the formula II at 30°–32° C., until 62–65% of the desired 5-chloro-3-chlorosulphonyl-2-thiophene-carboxylic acid ester of formula I is formed.

5. Process according to claim 1 wherein the activation of iron is performed at 10°–50° C.

6. Process according to claim 1 wherein the activation of iron is performed at 24° to 28° C.

* * * * *